US00PP29877P3

(12) United States Plant Patent
Olesen

(10) Patent No.: US PP29,877 P3
(45) Date of Patent: Nov. 27, 2018

(54) MINIATURE ROSE PLANT NAMED 'POULPAR102'

(50) Latin Name: ***Rosa* hybrid**
Varietal Denomination: Poulpar102

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 51 days.

(21) Appl. No.: 15/330,287

(22) Filed: Sep. 6, 2016

(65) Prior Publication Data

US 2018/0070502 P1 Mar. 8, 2018

(51) Int. Cl.
*A01H 5/02* (2018.01)
*A01H 6/74* (2018.01)

(52) U.S. Cl.
USPC ..... Plt./121
CPC ..... *A01H 5/02* (2013.01); *A01H 6/749* (2018.05)

(58) Field of Classification Search
USPC ..... Plt./121
See application file for complete search history.

*Primary Examiner* — Keith O. Robinson

(57) ABSTRACT

A new garden rose plant of the Miniature class which has abundant, pink blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulpar102'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar102', originated as a single seedling from the stated cross.

The new variety may be distinguished from its male pollen parent and female seed parent primarily by the following characteristics. The male pollen parent plant has near white flowers, while the new variety has pink blend flowers. The female seed parent plant has apricot colored flowers, while the new variety has pink blend flowers.

The objective of the hybridization of this rose variety was to create a new and distinct variety for garden use with unique qualities, such as:

1. Uniform and abundant pink blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar102' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar102' was selected in the spring of 2012 by the inventor as a single plant from the progeny of the aforementioned hybridization.

Asexual reproduction of 'Poulpar102' by traditional budding and rooted cuttings was first done by Mogens N. Olesen in the nursery in Fredensborg, Denmark in July, 2012. This initial and other subsequent asexual propagations conducted in controlled environments have demonstrated that the characteristics of 'Poulpar 102' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar102'.

Specifically illustrated in FIG. 1 are open flowers viewed above and from the side, sepals detached showing the receptacle and reproductive flower parts, and flower petals detached.

DETAILED DESCRIPTION OF THE VARIETY

Figure 1:
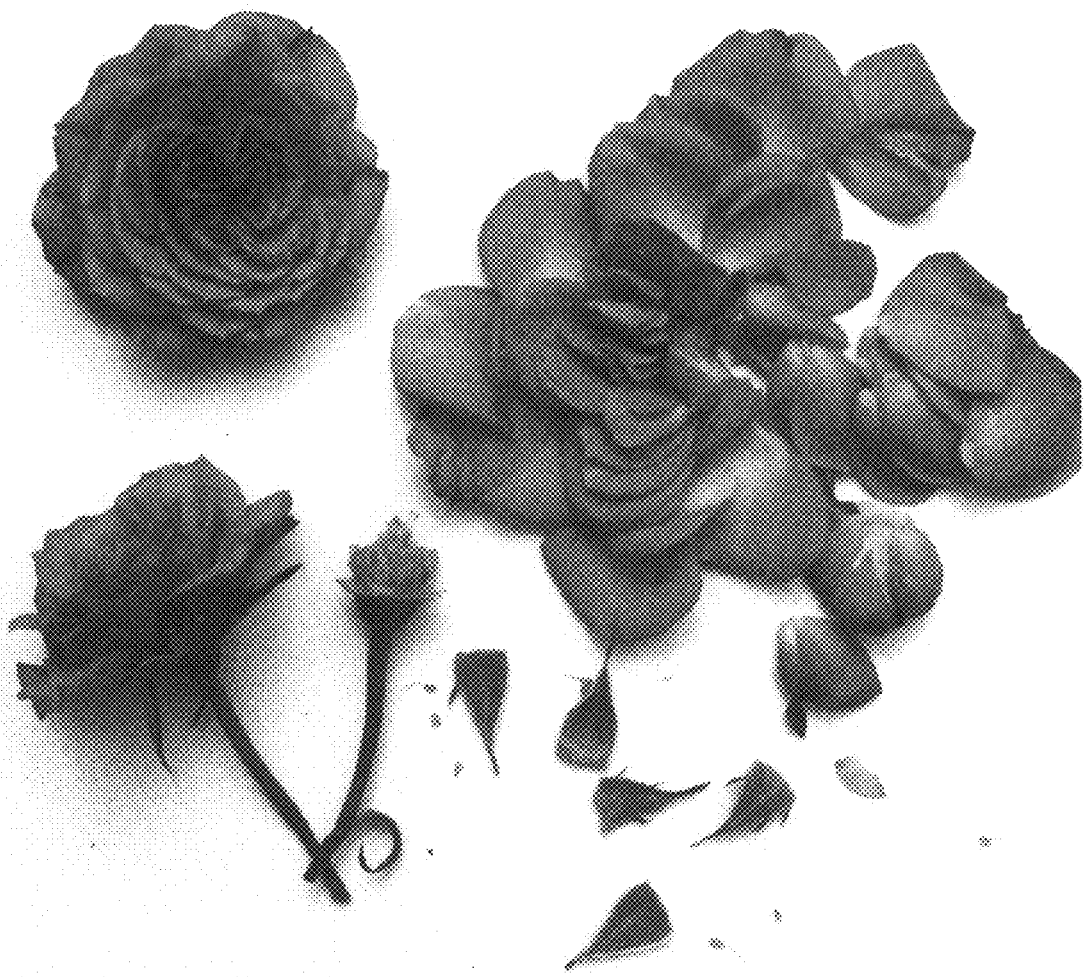
Figure 2:
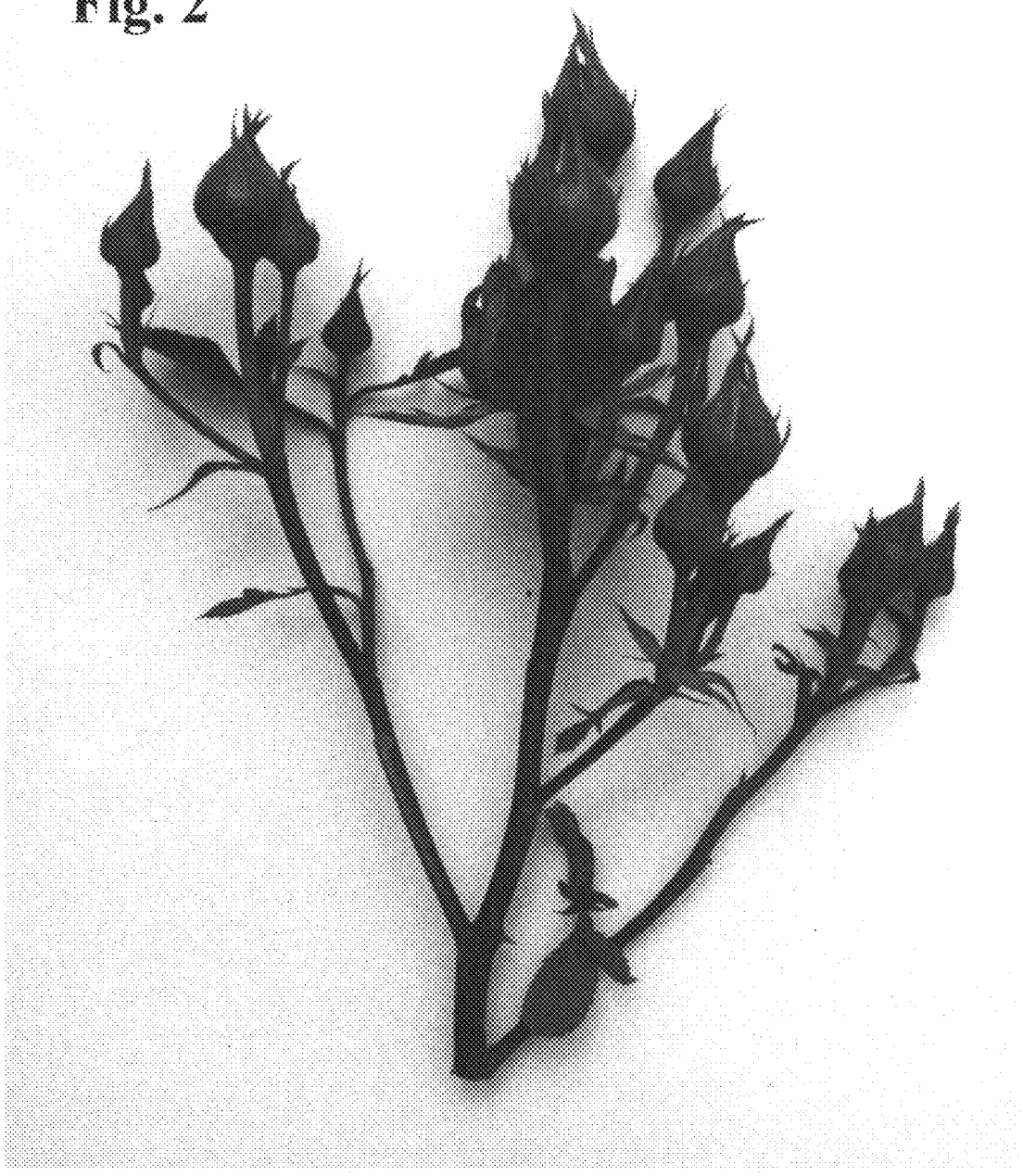
FIG. 2 shows a cluster of unopened flower buds and bare stems.
Figure 3:
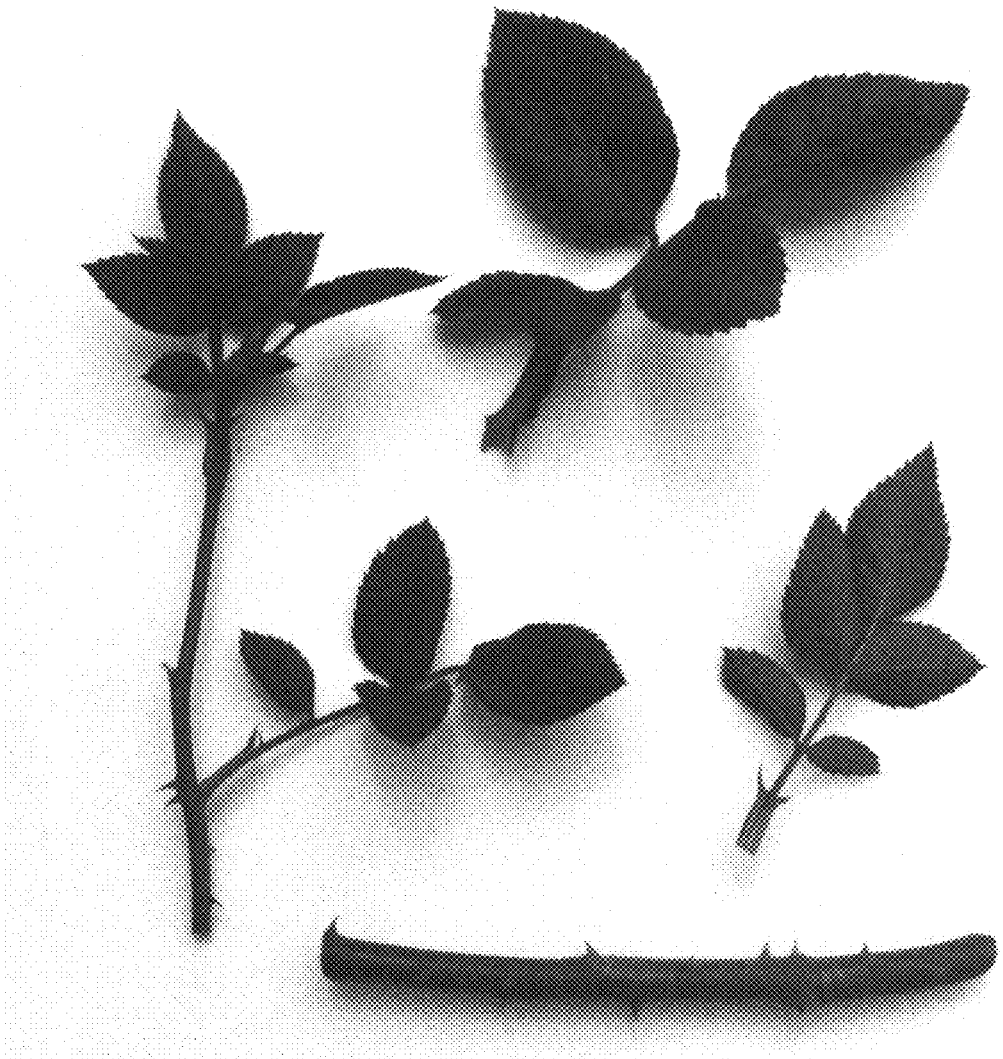
FIG. 3 shows leaves and bare stems. Plants shown are 2 years of age.

The following is a description of 'Poulpar102', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poultin', U.S. Plant Pat. No. 10,164 are compared to 'Poulpar102' in Chart 1.

CHART 1

| | 'Poulpar102' | 'Poultin' |
|---|---|---|
| Petal Count | 90 | 20 to 25 |
| Flower Diameter | 52 mm | 44 to 50 mm |
| Upper petal surface coloration | Red-Purple Group N57A | Red-Purple Group 58B |

FLOWER AND FLOWER BUD

Blooming habit: Continuous.

Flower bud:

*Size*.—Upon opening, 12 mm in length from base of receptacle to end of bud. Bud diameter is 14 mm.

*Bud form*.—Ovoid.

*Sepal inner surface*.—Color: Yellow-Green Group 145B. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—20 mm long, 9 mm wide.

*Receptacle*.—Texture: Smooth. Size: 5 mm in height, 7 mm wide. Color: Yellow-Green Group 144A with intonations of Greyed-Red Group 180A. Shape: Campanulate.

*Pedicel*.—Surface: Smooth. Length: 25 mm. Diameter: 2 mm on average. Color: Yellow-Green Group 144A with intonations of Greyed-Purple Group 183C. Strength: Strong.

*Peduncle*.—Length: 1 to 8 cm. Diameter: About 2 mm. Color: Yellow-Green Group 144A with intonations of Greyed-Purple Group 183C. Texture: Smooth.

Flower bud development: Flower buds are borne in corymbs of about 5 flower buds per stem.

Flower bloom:

*Fragrance*.—None.

*Duration*.—The blooms have a duration on the plant of approximately 10 days. Petals fall cleanly away from plant after flowers have fully matured.

*Size*.—Flower diameter is 52 mm when open. Flower depth is 20 mm.

*Flower shape*.—Rosette. Very double flower with many slightly overlapping petals of different sizes.

Petalage: Under normal conditions, flowers have about 90 petals.

General tonality of flower: Open flowers are Red-Purple Group N57A.

Petal color:

*Upon opening, outer & inner petals*.—Upper surface: Red-Purple Group N57B. Lower surface: Red-Purple Group N57D.

*Basal petal spots, upon opening*.—Upper surface: White Group 155A. Lower surface: White Group 155A.

*After opening, inner & outer petals*.—Upper surface: Red-Purple Group N57B. Lower surface: Red-Purple Group N57D.

*Basal petal spots, after opening*.—Upper surface: White Group 155A. Lower surface: White Group 155A.

Petals:

*Petal reflex*.—Somewhat reflexed.

*Margin*.—Entire and uniform. Moderate undulations.

*Shape*.—Generally rounded. Apex shape: Rounded. Base shape: Acute.

*Size*.—About 25 mm (l)×23 mm (w).

*Texture*.—Smooth.

*Thickness*.—Average.

Reproductive flower parts:

*Pollen*.—None observed.

*Anthers*.—Size: 1 mm in length. Color: Greyed-Yellow Group 161D. Quantity: 32 on average.

*Filaments*.—Color: Yellow-White Group 158D. Length: 2 mm.

*Pistils*.—Length: 4 mm. Quantity: 20 on average.

*Stigmas*.—Color: Greyed-Yellow Group 160A.

*Styles*.—Color: Greyed-Yellow Group 160A.

*Location of stigmas*.—Superior in location relative to the length of the filaments and the height of the anthers.

*Hips*.—None Observed.

PLANT

Plant growth: Upright, bushy. Plants are 30 cm in height, and 30 cm wide.

Stems:

*Color*.—Juvenile growth: Yellow-Green Group 144B. Mature growth: Yellow-Green Group 144A.

*Length*.—On average, canes are 13 cm from the base of the plant to the flowering portion.

*Diameter*.—5 mm.

*Internodes*.—On mature canes about 20 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 4 mm.

*Shape*.—Upper portion is linear. Lower portion is concave.

*Color*.—Juvenile prickles: Greyed-Red Group 181B. Mature prickles: Greyed-Red Group 181B.

Plant foliage:

*Compound leaf*.—90 mm (l)×70 (w).

*Quantity*.—About 3 leaves per 10 cm of stem on average.

*Leaf bearing angle to the stem*.—60 degrees.

*Color of juvenile foliage*.—Upper side: Yellow-Green Group 144A with intonations of Greyed-Purple Group 183A. Lower side: Yellow-Green Group 144A with intonations of Greyed-Purple Group 183A.

*Color of mature foliage*.—Upper side: Yellow-Green Group 146A. Lower side: Yellow-Green Group 146B.

Plant leaves and leaflets:

*Stipules*.—Size: 13 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 15 mm. Diameter: 2 mm.

*Upper surface*.—Color: Yellow-Green Group 144A.

*Lower surface*.—Color: Yellow-Green Group 144A.

*Rachis*.—Length: 25 mm. Upper surface: Color: Yellow-Green Group 144A.

*Lower surface*.—Color: Yellow-Green Group 144A.

*Leaflet*.—Quantity: Normally 5 leaflets. Margins: Serrated. Size: On average terminal leaflets are 40 mm long, 25 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar102', substantially as illustrated and described herein, due to its abundant pink blend flowers, disease resistance, and extended period of bloom.

* * * * *

'Poulpar102'

'Poulpar102'

'Poulpar102'